United States Patent [19]

Ahmad et al.

[11] Patent Number: 5,427,791
[45] Date of Patent: Jun. 27, 1995

[54] EMBRYONAL VACCINE AGAINST NEWCASTLE DISEASE

[75] Inventors: Jamil Ahmad, Falcon Heights; Jagdev M. Sharma, Vadnais Heights, both of Minn.

[73] Assignee: Regents of the University of Minnesota, Minneapolis, Minn.

[21] Appl. No.: 125,619

[22] Filed: Sep. 23, 1993

Related U.S. Application Data

[63] Continuation of Ser. No. 925,527, Aug. 5, 1992.

[51] Int. Cl.$^6$ .......................... A61K 39/17; C12N 7/06
[52] U.S. Cl. .................. 424/214.1; 424/816; 435/235.1; 435/238
[58] Field of Search ...................... 424/89, 214.1, 816; 435/235.1, 238

[56] References Cited

U.S. PATENT DOCUMENTS

| | | | |
|---|---|---|---|
| 4,053,583 | 10/1977 | Gits et al. | 424/214.1 |
| 4,235,876 | 11/1980 | Gits et al. | 424/214.1 |
| 4,279,893 | 7/1981 | Kreimer et al. | 424/214.1 |
| 4,458,630 | 7/1984 | Sharma et al. | 119/6.8 |
| 4,714,678 | 12/1987 | Delgoffe et al. | 435/235.1 |
| 5,112,381 | 5/1992 | Trujillo | 504/117 |
| 5,118,502 | 6/1992 | Glisson et al. | 424/214.1 |

OTHER PUBLICATIONS

Pringle Genetic Characteristics of Conditional Lethal Mutants . . . , J. Virol., 1970, 5:559–67.
Tsips et al., Isolation and Preliminary . . . , J. Virol., 1976, pp. 848–855.
"Chicken Embreyonal Vaccination with Avian Infectious Bronchitis Virus" by P. S. Wakenell DVM, pp. 933–938, American Journal of Veterinary Research, vol. 47, No. 4.
"Newcastle Disease Virus, An Evolving Pathogen" by Robert Hanson, U of Wis. Press., 1964, p. 201.
Gelcnzei, E. et al., (1960), Am. J. Res., Nov.; 987–991.
Lana, D. P. et al., (1988), Avian Dis., 32:273–281.
Solsaris, M. et al., (1989), Avian Dis., 33:248–253.
Kelleher, C. F. et al., (1988), Avian Dis., 32:342–346.
Sharma, J. M. et al., (1982), Avian Dis., 26:134–149.
Auerbach, C., (1967), Science, 158:1141–1147.

Primary Examiner—Christine M. Nucker
Assistant Examiner—Julie Krsek-Staples
Attorney, Agent, or Firm—Vidas, Arrett & Steinkraus

[57] ABSTRACT

Embryonal vaccination of fowl against Newcastle disease is accomplished with ethyl methane sulfonate modified NDV-B1 virus.

5 Claims, No Drawings

EMBRYONAL VACCINE AGAINST NEWCASTLE DISEASE

This is a continuation of application Ser. No. 07/925,527 filed on Aug. 5, 1992.

FIELD OF THE INVENTION

This invention relates to vaccines to protect chickens from Newcastle disease.

DESCRIPTION OF THE RELATED ART

Newcastle disease (ND) continues to have substantial economic impact on the poultry industry throughout the world. The virus is ubiquitous and commercial chickens must be protected against exposure to virus present in the environment. Currently, ND virus (NDV) vaccine is administered to hatched chicks through drinking water, aerosol, eye drop or by parenteral routes. Studies within the last few years have shown that live vaccines that are routinely administered to hatched chickens may also be injected into embryonated eggs during late stages of embryonation. Chicks hatching from vaccine injected eggs show resistance against homologous viruses at hatch. Several commonly used vaccines such as turkey herpesvirus (HVT), infectious bronchitis virus (IBV), and infectious bursal disease virus (IBDV) may be used as embryo vaccines. *Avian Dis* 1982; 26:134–149; *Am J Vet Res* 1986; 47:933–938; *Avian Dis* 1985; 29:1155–1169.

In chickens, early protection from virulent Marek's disease virus has been achieved through embryo vaccination (EV). Similar observations have been reported in mammalian fetuses with several pathogens such as *E. coli, Brucella abortus, Mycobacterium bovis* and tetanus toxoid. *Am J Vet Res* 1973; 34:737–741; *Am J Vet Res* 1978; 39:1742–1747.

Newcastle disease virus is an acute, highly contagious disease of chickens, turkeys and guinea fowls of all ages. In endemic areas, birds must be protected against the disease by vaccination. Active immunity against NDV has been known to appear in newly hatched chicks even in the presence of maternal antibodies. Thus early immunization against NDV through EV may be desirable.

The use of chemical mutagenic agents to produce living organisms with novel properties is now well established and has received an increased attention especially in the development of new vaccines. *Science* 1967; 158:1141–1147.

Previous studies have shown that EMS treatment of the T4 phage resulted in a stable mutant. *Proc Natl Aca Sci* 1960; 46:1585–1594. Similarly, treatment of a virulent Brucella strain with an alkylating agent, diethyl sulphate (DES), rendered the bacterium less virulent but retained its immunogenicity. *J Med Microbiol* 1989; 30:143–148.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

Protection against Newcastle disease in fowl, especially by injecting vaccines at the embryo stage, is highly desirable. Commercial use of embryo vaccination (EV) technology may reduce labor costs because semi-automatic machines with multiple injection heads may be used to administer vaccine simultaneously into a large number of eggs. Other possible advantages of EV include early neonatal resistance and administration of a uniform dose of vaccine into each egg. Our objective was to examine the possibility of protecting chickens against ND by EV. Preliminary studies revealed that the B1 strain of NDV (NDV-B1) that is routinely used as a vaccine in newly hatched chicks was lethal for 18-day-old embryos. Thus, the available techniques could not be used with this virus to protect birds.

We attempted EV in chickens with NDV-B1. This vaccine strain is non-pathogenic for hatched chicks and is routinely used as a post-hatch vaccine in commercial flocks. Because NDV-B1 was lethal for embryos, a workable modification of NDV-B1 was necessary to render it safe as an embryo vaccine. Previous attempts to modify NDV-B1 by passage in embryonating eggs or in cell culture or treatment of the virus with physical means (temperature or radiation) either increased the pathogenicity of the virus for 9–10-day old embryos or resulted in loss of immunogenicity for chickens. *Avian Dis* 1989; 33:248–253; *Am J Vet Res* 1960; Nov. 987–991; *Newcastle Disease Virus. The University of Wisconsin Press.* 1964.

The vaccine we have developed, namely NDV-B1-EMS is useful to protect any avian species that may contract Newcastle disease, including, but not limited to chicken, turkey, pheasants and guinea fowl. The vaccine may be given in a mixture of vaccines against other avian diseases. The NDV-B1-EMS virus may be given at various ages of the embryo or hatched bird, and may be given in multiple staged injections.

We provide a modified virus through the use of ethyl methane sulfonate (EMS) that is non-pathogenic for late stage embryos or hatched chicks and retains immunogenicity. This simple method of modifying the NDV-B1 strain of Newcastle virus results in an acceptable vaccine that can be used for EV. This chemically induced mutation may be replicated consistently. This method of using EMS to modify NDV-B1 virus generates an effective virus for use as a vaccine when employed.

The invention provides a vaccine and method for vaccinating fowl embryos or hatched fowl against Newcastle disease. The vaccine may be live or killed and may be presented in any of the standard formulations, including freeze-dried forms.

DESCRIPTION OF THE PREFERRED EMBODIMENTS

Materials and Methods

Newcastle Disease Virus

NDV-B1 was obtained from the American Type Culture Collection (ATCC), Rockville, Md. under reference number NDV-B1, VR 108, lot 11D. The virus was propagated in 9-to 10-day-old specific pathogen free (SPF) embryonated chicken eggs. Allantoic fluid was harvested after 48 hours of incubation and stored at $-70°$ C. The stock virus was titrated in 9-to 10-day-old SPF eggs to determine the embryo lethal doses ($ELD_{50}$) per ml. See Reed L J, Muench H. *A simple method of estimating fifty percent end point. Am J Hygiene* 1938; 27:493–497. The hemagglutination (HA) titer was determined by quantitating the ability of the virus to agglutinate chicken erythrocytes. HA are hemagglutination units of virus expressing the highest dilution capable of causing complete agglutination of chicken erythrocytes. Buxton A, Fraser G. *Animal Microbiology* 1977; vol. 2. Blackwell Scientific Pub. London. For challenge, two velogenic, neurotropic strains of NDV were used: NDV-1519 (Titer, $10^{8.6}$ ELD$_{50}$/ml) or GB-Texas (Titer, $10^{8.2}$ ELD$_{50}$/ml). *Avian Dis* 1988; 32:342–346; *Avian Dis* 1988; 32:273–281.

Chemical Treatment of NDV-B1

The stock of NDV-B1 was treated with several chemicals (all purchased from Sigma Chemical Co., St. Louis, Mo.) in an effort to modify the virus and render it safe for 18-day-old embryonated eggs. The procedures for the chemical treatment of viruses have been described previously. Pringle C R. *Genetic characteristics of conditional lethal mutants of Vesicular stomatitis virus induced by 5-Fluorouracil, 5-Azacytadine and Ethyl Methane sulfonate; J Vir.* 1970; 5:559–567; Tsipis J E, Bratt M A; *Isolation and preliminary characterization of temperature sensitive mutants of Newcastle disease virus. J Vir* 1976; 18:848–855. Brief descriptions of each treatment are presented below:

i. Nitrosoguanidine

Nitrosoguanidine was added to a final concentration of 100 ug/ml of the stock virus and incubated at 25° C. for 30 min. Nitrosoguanidine was removed from the mixture by dialysis against Tris-buffer and supplemented with 2% calf serum.

ii. Ethyl Methane Sulfonate (EMS)

One hundred ul of EMS were added to 10 ml of 0.5M sodium acetate and shaken for 2 min at 31° C. An equal volume of virus was added to the mixture and incubated at 31° C. for 30 min. The reaction was stopped by 10-fold dilution into 1% (w/v) sodium thiosulphate in phosphate buffer saline (PBS). After 2 hours at 4° C., 2% calf serum was added. The NDV-B1-EMS virus was stored at −70° C.

iii. 5-Fluorouracil (5-FU) and 5-Azacytadine (5-AZ)

Four hundred ug of 5-FU or 5-AZ individually or in combination were added to 1 ml of the virus and the mixture was incubated at 36° C. for 11 hours. The HA and the ELD$_{50}$ titer of each chemically treated virus was determined as described above.

Eggs and Chickens

SPF chicken eggs at embryonation day (ED) 18 and day-old SPF chicks were obtained from Hyvac Laboratory Egg Company, Gowrie, Iowa. The parent flock was free of common bacterial and viral pathogens including NDV, IBV, IBDV, arian adenoviruses and avian herpesviruses. The commercial hatching eggs were purchased from a local source. The parent commercial flocks had been immunized against NDV and the progeny chicks hatched with maternal anti-NDV antibodies. Embryonated eggs in different treatment groups were hatched in separate Horsfall-Bauer type isolation units supplied with biologically filtered air. Similar isolation units were used to rear experimental chickens.

Embryo Vaccination

An inoculum of 100 ul was injected into each egg at ED 18 according to the procedure described earlier. Sharma J M, Burmester B R. *Resistance to Marek's Disease at hatching in chickens vaccinated as embryos with the Turkey herpes virus. Avian Dis* 1982; 26:134–149. A 1 ml syringe attached to a 1½×22 gauge hypodermic needle was used. The entire length of the needle was inserted into the egg through a hole punched in the large end of the egg shell. The hole was not sealed following inoculation.

Serology

Sera were tested for hemagglutination inhibition (HI) antibodies to NDV by the beta-microtest. Buxton A, Fraser G. *Animal Microbiology* 1977, vol. 2. *Blackwell Scientific Pub. London.* The HI titer was expressed as the reciprocal of the highest dilution of serum causing complete inhibition of hemagglutination of chicken erythrocytes. A geometric mean titer (GMT) was determined for the sera within each group. Burgh M A. *A simple method of recording and analyzing serological data. Avian Dis.* 1978; 22:362–365.

Virus Isolation from Tissues

The tissue homogenates from lungs and spleen of hatched or unhatched embryos were inoculated into 10-day-old embryonated commercial chicken eggs. The allantoic fluids harvested 72–96 hours after inoculation were tested for HA activity as previously described. Halvorson D A, Karunakaran D, Senne D, Kelleher C, Bailey C, Abraham A, Hinshaw V, Newman J A. *Epizootology of avian Influenza-simultaneous monitoring of sentinel ducks and turkeys in Minnesota. Avian Dis* 1983; 27:77–85.

Experimental Design

Expt. 1

The effect of NDV-B1 on chicken eggs at ED 18 was examined. Ten SPF embryonated chicken eggs per group were injected with the following doses (log ELD$_{50}$/egg): 2.8, 1.8, 0.8, and 0.0. Each of ten day-old SPF chickens was injected with $10^{5.8}$ ELD$_{50}$ of NDV-B1 by the oculonasal route. Virus-injected and diluent-injected eggs were observed for hatchability and chicks were observed for survival until 1 week of age.

Expt. 2

The effect of chemical treatment on NDV-B1 and the response of chicken embryos to chemically treated viruses were examined. Each chemically treated virus preparation and untreated control preparation was titrated for HA or ELD$_{50}$. Various virus preparations were injected into embryonated SPF eggs at ED 18. Eggs were observed for hatchability and the hatched chicks were observed for survival until 1 week of age.

Expt. 3

We determined if NDV-B1 treated with EMS (NDV-B1-EMS) could be recovered from the tissues of chicks hatching from eggs inoculated with the virus at ED 18. In Trial 1, each of 20 SPF chicken eggs at ED 18 was injected with 2048 HA units of NDV-B1-EMS. Each of 20 eggs was injected with 2048 HA units of NDV-B1 and a third group of 10 eggs received virus-free diluent. Virus isolation was attempted from lung and spleen of chickens or embryos of all 3 groups. Trial 2 was similar to Trial 1 in design except that 2048 HA units of each of the 2 viruses were used in groups of 5 embryonated commercial eggs. Virus isolation was attempted from pooled samples from lung and spleen of each chicken or embryo.

Expt. 4

In this experiment we examined the ability of NDV-B1-EMS to induce antibodies and resistance against ND. Three trials were conducted. In Trial 1, ten commercial eggs at ED 18 were inoculated with NDV-B1-EMS (2048 HA units/egg) and 8 eggs with virus-free diluent as negative controls. Simultaneously with the above 2 groups, 1-day-old commercial chickens were inoculated with NDV-B1 (2048 HA units/chicken) by the oculonasal route as positive controls. Chickens hatching from virus-infected and uninfected eggs and chickens exposed to NDV-B1 at hatch were tested for anti-NDV HI antibodies weekly from 1 to 4 weeks of age. Chicks from embryo-inoculated, post hatch inoculated and uninoculated control chickens were challenged at 4 weeks intraocularly with NDV-1519 ($10^{4.0}$ $ELD_{50}$/chicken). The experiment was terminated 1 week following the challenge and surviving chickens were necropsied and examined for gross lesions of ND. Alexander, D J. *In Diseases of Poultry*, by Calnek W, Barnes J H, Beard C W, Reid W M, Yoder H W Jr. 1991; 9th ed. *Iowa state Uni. Press*, Ames, Iowa.

In Trial 2, groups of commercial chicken eggs were inoculated with 2048, 409 and 204 HA units of NDV-B1-EMS per egg. One group of eggs was inoculated with virus free diluent. Chickens hatching from all groups were examined weekly up to 4 weeks of age for HI antibody. At 4 weeks of age, vaccinated and unvaccinated chickens were challenged with NDV-1519 ($10^{4.0}$ $ELD_{50}$/chicken). Challenge response was observed as in Trial 1 above.

In Trial 3, the ability of NDV-B1-EMS to immunize hatched chickens against ND was determined. Four 4-week-old SPF chickens, lacking detectable antibodies to NDV were inoculated by the oculonasal route with NDV-B1-EMS (10240 HA units per chicken). Four hatchmates received NDV-B1 (10240 HA units/chicken) by the oculonasal route and 4 additional hatchmates received virus-free diluent by the same route and served as controls. Four weeks following virus-inoculation, chickens in all 3 groups were examined for anti-NDV antibodies and then challenged intraocularly with the GB-Texas strain of virulent NDV ($10^{4.0}$ $ELD_{50}$/chicken). The trial was terminated 1 week after challenge and survivors were necropsied and examined for gross lesions of ND.

Expt. 5

The minimum protective dose$_{50}$ of NDV-B1-EMS in SPF and commercial eggs at ED 18 was determined. In Trial 1, groups of SPF and commercial eggs were inoculated with 3162, 316.2, 31.62, 3.162 and 0.316 $ELD_{50}$ of NDV-B1-EMS or NDV-B1. Control eggs received virus free diluent. At 4 weeks of age, chickens hatching from vaccinated and unvaccinated eggs were tested for antibody to NDV and challenged with the GB-Texas ($10^{4.0}$ $ELD_{50}$/chicken). Minimum protective dose$_{50}$ (MPD$_{50}$) of both SPF and commercial chickens was determined by using logit transformation analysis. Traemor D H Jr. *Applied Categorical Data Analysis*. Mercel Dekker Inc. New York. 1987; 239-245. Trial 2 was a repeat of Trial 1 except commercial eggs were injected with 1000, 100, 10, 1.0 and 0.1 $ELD_{50}$ of NDV-B1-EMS or NDV-B1.

Results

Response of 18-Day-Old Chicken Embryos to NDV-B1 (Expt. 1)

As shown in Table 1, all doses of NDV-B1 used were lethal for SPF embryos. The hatchability of virus-injected but not of diluent-injected eggs was extremely poor. None of the chicks hatching from virus-injected groups survived until 1 week of age. As expected, NDV-B1 was not pathogenic for hatched chicks. All chickens given $10^{5.8}$ $ELD_{50}$ of the virus at hatch remained healthy during the course of experiment.

TABLE 1

Pathogenic effect of NDV-B1 on SPF eggs inoculated at embryonation day 18 (ED 18). (Expt. 1)

| Inoculum | Time of inoculation | Dose log $ELD_{50}$/ egg or chick | No. hatched/No. inoculated | No. survived*/No. inoculated |
|---|---|---|---|---|
| NDV-B1 | ED 18 | 2.8 | 0/10 | 0/10 |
| | ED 18 | 1.8 | 2/10 | 0/10 |
| | ED 18 | 0.8 | 2/10 | 0/10 |
| Diluent | ED 18 | 0.0 | 10/10 | 10/10 |
| NDV-B1 | at hatch | 5.8 | N.A | 10/10 |

*Chickens observed until 7-day-old
N.A = Not applicable

Characteristics of Chemically-Treated Viruses (Expt. 2)

Effect of Chemical Treatment on Virus Titer and Hatchability

A slight decrease in HA and $ELD_{50}$ titer was seen in viruses treated with nitrosoguanadine, 5-FU and 5-AZ (Table 2). Treatment with EMS resulted in a 4 fold reduction in the HA titer and about 100 fold reduction in the $ELD_{50}$ titer. NDV-B1 treated with nitrosoguanadine, 5-FU and 5-AZ remained pathogenic for embryonated chicken eggs at ED 18 and adversely affected hatchability and survival. Eighty percent of the eggs injected with NDV-B1-EMS hatched and 14 of 16 hatched chickens survived through the observation period of 7 days whereas, 100 percent control hatched and lived. These results indicated that treatment of NDV-B1 with EMS reduced the pathogenicity of the virus for 18-day-old embryonated chicken eggs. Further studies were initiated to examine the suitability of NDV-B1-EMS as an embryo vaccine against ND.

TABLE 2

The effect of chemical treatment of NDV-B1 on virus titer and the response of 18-day-old SPF chicken embryos. (Expt. 2)

| Chemical used to treat NDV-B1 | Virus titer/ml | | Response to inoculation at embryonation day 18 | | |
|---|---|---|---|---|---|
| | HA units | log $ELD_{50}$ | No. eggs hatched/ No. inoculated | % eggs hatched | No. chicks survived for 1 week/No. hatched |
| None | 40960 | 5.8 | 0/20 | 0 | NA |
| Nitrosoguanidine | 20480 | 5.2 | 2/20 | 10 | 0/2 |
| Ethyl methane sulfonate | 10240 | 3.9 | 16/20 | 80 | 14/16 |
| 5-Fluorouracil | 20480 | 5.0 | 6/25 | 24 | 2/6 |
| Azocytadine | 20480 | 5.1 | 0/20 | 0 | NA |
| 5-Fluorouracil + Azocytadine | 20480 | 5.0 | 0/20 | 0 | NA |
| None (diluent control) | 0 | 0.0 | 10/10 | 100 | 10/10 |

NA = Not applicable
HA = hemagglutination

Isolation of NDV-B1-EMS from Tissues of Chicks (Expt. 3)

NDV-B1-EMS was isolated from lung and spleen of chickens hatching from SPF or commercial eggs inoculated with the virus at ED 18 (Table 3). Day-old chicks hatching from SPF and commercial eggs had HI (GMT) of 0 and 36.8 respectively. These results provided preliminary indication that the modified virus infected and replicated in tissues of embryos in the absence and presence of maternal antibodies against NDV. The virus was also isolated from lung and spleen of embryos injected with NDV-B1. Embryos and chicks from uninoculated control groups were negative for virus isolation.

nated chickens had anti-NDV antibodies at 4 weeks of age and all resisted a challenge with virulent NDV.

In Trial 3, groups of 4-week-old SPF chickens were exposed to NDV-B1-EMS and NDV-B1. Both viruses elicited an antibody response and all vaccinated chickens were resistant to exposure to virulent NDV 4 weeks following vaccination. Data of Experiment 4 indicated that NDV-B1-EMS was an effective vaccine for embryonated eggs at ED 18 and for 4-week-old chickens.

TABLE 4

Antibody production and resistance against virulent NDV in chickens given NDV-B1-EMS and NDV-B1 as embryo or after hatch (Expt. 4)

| Trial # | Type of eggs or chickens | Virus inoculation inoculum | Dose of virus egg or chick HA units | Age at inoc. | No. inoculated | Prechallenge HI antibodies +/tested | GMT* | No. died following challenge/No. challenged** |
|---|---|---|---|---|---|---|---|---|
| 1 | Commercial | NDV-B1-EMS | 2048 | ED 18 | 10 | 10/10 | 24.3 | 0/10 |
|   |            | NDV-B1     | 2048 | at hatch | 10 | 10/10 | 18.4 | 0/10 |
|   |            | Diluent    | 0    | ED 18 | 8  | 0/8   | 0.0  | 8/8 |
| 2 | Commercial | NDV-B1-EMS | 2048 | ED 18 | 8  | 8/8   | 24.3 | 0/8 |
|   |            |            | 409  | ED 18 | 8  | 8/8   | 13.0 | 0/8 |
|   |            |            | 204  | ED 18 | 8  | 8/8   | 7.0  | 0/8 |
|   |            | Diluent    | 0    | ED 18 | 8  | 0/8   | 0.0  | 8/8 |
| 3 | SPF        | NDV-B1-EMS | 10240 | 4-week | 4 | 4/4   | 68.6 | 0/4 |
|   |            | NDV-B1     | 10240 | 4-week | 4 | 4/4   | 60.0 | 0/4 |
|   |            | Diluent    | 0    | 4-week | 4 | 0/4   | 0.0  | 4/4 |

*geometric mean titer
**$10^4$ $ELD_{50}$ of GB-Texas NDV per chicken intraocularly
ED embryonation day, SPF specific pathogen free

TABLE 3

Virus isolation from tissues following inoculation with NDV at embryonation day 18 (Expt. 3)

| Trial # | Type of chicken | Inoculum | Dose/egg HA units | Hours post-inoculation | Virus isolation from tissues* lung | spleen | lung + spleen (pooled) |
|---|---|---|---|---|---|---|---|
| 1 | SPF | NDV-B1 | 1024 | 48 | 20/20** | 19/20 | NT |
|   |     | NDV-B1-EMS | 1024 | 96 | 14/20 | 12/20 | NT |
|   |     | Virus free diluent | 0 | 96 | 0/10 | 0/10 | NT |
| 2 | Commercial | NDV-B1 | 2048 | 72 | NT | NT | 5/5 |
|   |            | NDV-B1-EMS | 2048 | 96 | NT | NT | 4/5 |
|   |            | Virus free diluent | 0 | 96 | NT | NT | 0/5 |

*Tissue homogenate inoculated in 9 to 10 day-old embryos
**No. embryos or chicks positive/No. examined
NT Not tested Efficacy of NDV-B1-EMS as an Embryo Vaccine (Expt. 4)

Results of 3 trials are presented in Table 4. In Trial 1, all chicks hatching from eggs inoculated with NDV-B1-EMS had HI antibodies at 4 weeks of age. Positive controls given NDV-B1 at hatch were also positive for antibodies at 4 weeks. The uninoculated control group was free of detectable antibodies thus indicating that maternal antibodies had reached undetectable levels by 4 weeks of age and that the antibodies in virus-exposed groups were induced by the inoculated virus. All chickens vaccinated either as embryos or at hatch were protected against challenge with virulent NDV whereas all unvaccinated chickens died within 1 week of challenge. These data showed that NDV-B1-EMS was effective as an embryo vaccine because the virus induced resistance against challenge exposure. No gross abnormalities were detected at necropsy in the vaccinated chickens that survived the virulent virus challenge.

Similar results were obtained in Trial 2 in which NDV-B1-EMS was used at 3 dose levels. All vacci- Protective Efficacy of Graded Doses of NDV-B1-EMS Vaccine (Expt. 5)

The results are shown in Table 5. In Trial 1, the response to graded doses of NDV-B1-EMS and NDV-B1 were simultaneously compared in embryonated eggs from SPF and commercial flocks. The HI GMT in SPF and commercial chicks at hatch was 0 and 42.6 respectively. The highest dose tested for both viruses was 3162 $ELD_{50}$/egg. As expected, the hatchability and survival rate were better with NDV-B1-EMS than with NDV-B1. Chicks hatching from eggs given 3.16 $ELD_{50}$ or higher concentration of either virus induced antibody and/or resistance to challenge. Based on the protection results in Trial 1 presented in Table 5, $MPD_{50}$ for NDV-B1-EMS in SPF and commercial eggs was calculated to be 10.77 and 17.70 $ELD_{50}$ respectively. All unvaccinated SPF and commercial chickens were negative for anti-NDV antibodies and succumbed to challenge with virulent NDV. In Trial 2, NDV-B1-EMS and NDV-B1 in doses of 1000 to 1.0 $ELD_{50}$/egg were protective against virulent NDV challenge. A dose of 0.1 $ELD_{50}$ was partially protective with both viruses. NDV-B1 reduced hatchability of commercial embryonated eggs, although this effect was not as severe as in SPF eggs used earlier in Experiment 1 (Table 1).

TABLE 5

| Trial # | Type of vaccine | Dose ELD$_{50}$ per egg | No. chicks hatched & survived/No. inoculated SPF | No. chicks hatched & survived/No. inoculated Commercial | HI antibody at 4 weeks (GMT)* SPF | HI antibody at 4 weeks (GMT)* Commercial | Challenge response** No. dead/No. inoculated SPF | Challenge response** No. dead/No. inoculated Commercial |
|---|---|---|---|---|---|---|---|---|
| 1 | NDV-B1-EMS | 3162 | 5/10 | 2/7 | 16.0 | 14.9 | 0/5 | 0/2 |
|   |            | 316.2 | 7/10 | 4/7 | 6.1 | 5.7 | 0/7 | 0/4 |
|   |            | 31.62 | 9/10 | 5/7 | 7.0 | 6.5 | 0/9 | 0/5 |
|   |            | 3.16 | 10/10 | 6/7 | <2 | <2 | 5/10 | 4/6 |
|   |            | 0.31 | 10/10 | NA | 0.0 | NA | 10/10 | NA |
|   | NDV-B1 | 3162 | 0/10 | 2/7 | NA | 11.3 | NA | 0/2 |
|   |        | 316.2 | 0/10 | 0/7 | NA | NA | NA | NA |
|   |        | 31.62 | 1/10 | 0/7 | 4.0 | NA | 0/1 | NA |
|   |        | 3.16 | 3/10 | 4/7 | 2.1 | 2.3 | 1/3 | 0/4 |
|   |        | 0.31 | 7/10 | NA | 0.0 | NA | 6/7 | NA |
|   | Diluent | — | 9/10 | 6/7 | 0.0 | 0.0 | 9/9 | 6/6 |
| 2 | NDV-B1-EMS | 1000 | — | 9/10 | — | 34.3 | — | 0/9 |
|   |            | 100 | — | 9/10 | — | 26.0 | — | 0/9 |
|   |            | 10 | — | 10/10 | — | 18.4 | — | 0/10 |
|   |            | 1 | — | 9/10 | — | 11.3 | — | 0/9 |
|   |            | 0.1 | — | 10/10 | — | 6.5 | — | 1/10 |
|   | NDV-B1 | 1000 | — | 3/10 | — | 32.0 | — | 0/3 |
|   |        | 100 | — | 8/10 | — | 27.0 | — | 0/8 |
|   |        | 10 | — | 5/10 | — | 26.0 | — | 0/5 |
|   |        | 1 | — | 9/10 | — | 12.1 | — | 0/9 |
|   |        | 0.1 | — | 10/10 | — | 4.3 | — | 3/10 |
|   | Diluent | — | — | 10/10 | — | 0.0 | — | 9/10 |

*Hemagglutination inhibition geometric mean titer
Commercial chicks having maternal antibody HI GMT (n = 5) at hatch in trial 1 and 2 was 34.3 and 207.9 respectively.
**Chickens were challenged with GB-Texas NDV 10$^4$ ELD$_{50}$ per bird intraoccularly
NA Not available

Discussion

The concept of embryo vaccination is based on an observation that chickens develop a level of immunological maturity well before hatching. Jankovic B D, Isakovic K, Lukic M L, et al. *Immunological capabilities of chicken. I. Relationship between the maturation of lymphoid tissues and occurrence of cell mediated immunity in the developing chicken embryo. Immunology* 1975; 29: 497–508; Well J C, Reynaud C A. *The chicken B-cell compartment. Science* 1987; 238: 1094–1098. Active immunity against NDV has been known to appear in newly hatched chicks even in the presence of maternal antibodies. Holmes H C. *Resistance of the respiratory tract of chickens to Newcastle disease virus infection following vaccination: The effect of passively acquired antibody on its development. J Comp Pathol* 1979; 89:11–19. Thus early immunization against NDV through EV may be desirable.

Of the several chemicals we examined, treatment with EMS made NDV-B1 suitable for 18-day-old embryos. When NDV-B1-EMS was inoculated into SPF or commercial eggs at ED 18, the eggs hatched and the hatched chicks survived. The hatched chicks developed anti-NDV antibodies and were resistant to challenge with virulent NDV 4 weeks later. NDV-B1-EMS apparently replicated in the tissues of the embryos because the virus was readily recovered from lung and spleen homogenates 96 hours following inoculation.

The mechanism by which EMS altered NDV-B1 is not known. It is possible that the chemical may have caused a point mutation in the NDV-B1 genome. EMS or other alkylating agents usually induce a non-revertable transition mutation that alters guanine-cytosine nucleotide bases with adenine-thymine. Auerbach C. *The chemical production of mutations. The effect of chemical mutagens on cells and their genetic material is discussed. Science* 1967; 158:1141–1147.

The chemical treatment with EMS may have caused a genetic lesion in the NDV-B1 virus that either reduced the pathogenicity of the virus or altered the kinetics of viral replication so that the rate of virus spread in the embryos was reduced, thus allowing the chick to hatch normally. Comparative molecular analyses of proteins and RNA from EMS-modified virus with its parent strain could provide an insight into the genetic basis of differences.

The exact route of infection of the embryo following inoculation in the eggs is not known. Previously we have shown that the inoculum injected according to the procedures used here generally gets deposited in the amniotic fluid. The infection likely occurs either through inhalation or ingestion of the infected amniotic fluid by the embryo. Inhalation and ingestion may stimulate local mucosal immunity as well as initiate a more generalized infection and immunity.

Presence of maternal antibodies to NDV did not appreciably influence the MPD$_{50}$ of NDV-B1-EMS. This result is consistent with published reports. Maternal antibodies may interfere with vaccinal immunity in ND although this effect is usually minimal. In our studies the commercial embryos generally had low levels of mAbs. Presence of massive titers of MAb may conceivably reduce the efficacy of NDV-B1-EMS. Of interest, was our finding that NDV-B1-EMS vaccine was also effective in 4-week old chickens. These chickens developed antibody to NDV and resisted challenge with virulent NDV. NDV-B1-EMS given at ED 18 or 4 weeks post hatch did not cause detectable lesions in chickens during the observation period of 5 weeks. The use of multiple vaccines in a single injection is highly desirable and is likely to save the cost of labor associated with vaccine administration. Previously, several multiple vaccines have been used to successfully immunize chicken embryos under laboratory conditions.

NDV-B1-EMS virus was deposited with the American Type Culture "Collection of 12301 Parklawn Drive, Rockville, Md. 20852 USA on Jul. 14, 1992 under accession number VR 2378". A pharmaceutically effective amount of the above described modified live virus may be employed along with a pharmaceutically acceptable carrier or diluent as a vaccine against Newcastle disease in fowl at the embryo or hatched stages. The usual dosage will be at least about 10 $ELD_{50}$/ml for SPF and 17 $ELD_{50}$/ml for commercial eggs.

As stated previously, the preferred administration is according to the teachings of U.S. Pat. No. 4,279,893, the disclosure of which is incorporated herein by reference. Although injection into the egg at 18 days is the preferred route, intranasal, intramuscular, subcutaneous or other parenteral administration into hatched chicks is acceptable.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A vaccine composition against Newcastle fowl disease comprising a modified live virus strain NDV-B1-EMS deposited Jul. 14, 1992 with the American Type Culture Collection, reference number VR2378 and a pharmaceutically acceptable diluent.

2. A process for vaccinating fowl embryos against Newcastle disease virus comprising the step of inoculating avian embryonated eggs with an injection of at least 3 $ELD_{50}$/ml ethyl methane sulfonate-modified NDV-B1 virus.

3. A vaccine against Newcastle disease comprising NDV-B1 virus modified by treatment with ethyl methane sulfonate and having a $MPD_{50}$ within the range of from about 10 to about 18 $ELD_{50}$/ml.

4. A method of immunizing fowl against Newcastle disease virus comprising administering to avian embryonated eggs an immunizing effective amount of a composition of claim 1.

5. In an inactivated vaccine ready for use against symptoms in poultry by Newcastle disease virus (ndv), characterized in that the vaccine contains an ethyl methane sulfonate inactivated Newcastle disease virus derived from NDV-B1 virus, the unmodified virus being deposited under the ATCC reference number NDV-B1, VR 108, lot 11D, said vaccine containing liquid having a titre of over about 2 $ELD_{50}$/ml.

* * * * *